(12) United States Patent
Yokosuka (10) Patent No.: US 8,512,319 B2
(45) Date of Patent: Aug. 20, 2013

(54) OPHTHALMIC LASER TREATMENT APPARATUS

(75) Inventor: Hiroki Yokosuka, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 63 days.

(21) Appl. No.: 13/337,915

(22) Filed: Dec. 27, 2011

(65) Prior Publication Data

US 2012/0184857 A1 Jul. 19, 2012

(30) Foreign Application Priority Data

Dec. 28, 2010 (JP) ................................. 2010-291489

(51) Int. Cl.
*A61B 18/18* (2006.01)

(52) U.S. Cl.
USPC ................... 606/4; 606/10; 351/206; 600/476

(58) Field of Classification Search
USPC ........ 600/473–480; 351/206–246; 606/4–10
See application file for complete search history.

(56) References Cited

U.S. PATENT DOCUMENTS

| | | | | |
|---|---|---|---|---|
| 6,585,722 B1 * | 7/2003 | Abe | ................................. | 606/4 |
| 6,869,428 B2 * | 3/2005 | Sagehashi et al. | ................. | 606/4 |
| 6,932,807 B1 * | 8/2005 | Tomita et al. | .................... | 606/10 |
| 7,229,435 B2 * | 6/2007 | Nakamura | ......................... | 606/4 |
| 2002/0007178 A1 * | 1/2002 | Donitzky | ........................... | 606/5 |
| 2002/0165525 A1 * | 11/2002 | Nakamura | ......................... | 606/4 |
| 2004/0057119 A1 * | 3/2004 | Sagehashi et al. | ............. | 359/618 |
| 2004/0102765 A1 * | 5/2004 | Koenig | .............................. | 606/5 |
| 2005/0080467 A1 | 4/2005 | Abe | | |
| 2009/0157062 A1 * | 6/2009 | Hauger et al. | ..................... | 606/5 |
| 2009/0171325 A1 * | 7/2009 | Koenig | .............................. | 606/5 |
| 2009/0298004 A1 * | 12/2009 | Rizoiu | ............................. | 433/29 |
| 2011/0245817 A1 * | 10/2011 | Yokosuka et al. | ................ | 606/4 |

FOREIGN PATENT DOCUMENTS

| | | |
|---|---|---|
| JP | A-2005-118166 | 5/2005 |
| JP | A-2006-524515 | 11/2006 |
| JP | A-2009-515654 | 4/2009 |
| WO | WO 2005/065116 A2 | 7/2005 |
| WO | WO 2007/059189 A2 | 5/2007 |

* cited by examiner

*Primary Examiner* — Sanjay Cattungal
(74) *Attorney, Agent, or Firm* — Oliff & Berridge, PLC (57) ABSTRACT

An ophthalmic laser treatment apparatus comprises: a main unit; a laser source; a hand-held cabinet; a laser delivery optical system for irradiating the laser beam in a predetermined irradiation pattern onto tissues of the patient's eye, the laser delivery optical system including: a fiber unit connecting the hand-held cabinet to the main unit; a scanner for deflecting an optical axis of the laser beam; and an image forming optical system for forming an image of the laser beam in the form of a spot on the tissues of the patient's eye; an irradiation pattern setting unit for setting an irradiation pattern of the treatment laser beam; a control unit for controlling drive of the scanner; and a beam combiner provided in the hand-held cabinet to make an observation optical path and an optical path of the laser delivery optical system coincident with each other.

10 Claims, 4 Drawing Sheets

OPHTHALMIC LASER TREATMENT APPARATUS

CROSS-REFERENCE TO RELATED APPLICATIONS

This application is based upon and claims the benefit of priority from the prior Japanese Patent Application No. 2010-291489, filed Dec. 28, 2010, the entire contents of which are incorporated herein by reference.

TECHNICAL FIELD

The present invention relates to an ophthalmic laser treatment apparatus for performing treatment by irradiating a laser beam to a patient's eye.

BACKGROUND ART

An ophthalmic laser treatment apparatus used for performing photocoagulation and others includes an irradiation optical system (a laser delivery) for irradiating a laser beam for treatment emitted from a laser source to a patient's eye. In use, this irradiation optical system is generally attached to a microscope unit having a binocular observation optical system. The microscope unit is placed on a table provided with a head supporting unit for stably holding the face (head) of a patient. The patient is subjected to a surgery while being in a sitting position with his/her face fixedly supported. On the other hand, for a recumbent patient who can not be subjected to a surgery in a sitting position, an operator often uses an apparatus in which an irradiation optical system is attached to a binocular indirect ophthalmoscope which is a visor-shaped observation unit. The operator wears the binocular indirect ophthalmoscope with the irradiation optical system on his/her head to conduct treatment (see Patent Document 1, for example).

Further, an ophthalmic laser treatment apparatus for photocoagulation and others is conventionally provided with an irradiation optical system for irradiating a laser beam by one spot at a time. Recently, in contrast, there is a proposed a laser treatment apparatus (a scanning-type photocoagulation apparatus) provided with a scanning unit including a galvano mirror and others in an irradiation optical system and arranged to scan a laser beam in the form of a spot on the tissues of a fundus in two dimensions (see for example Patent Documents 2 and 3). This apparatus enables irradiation of a plurality of spots in a short time, leading to shortening of surgery time, and resulting in lesser burden on both a patient and a doctor.

RELATED ART DOCUMENTS

Patent Documents

Patent Document 1: JP 2005-118166A (US2005/080467)
Patent Document 2: JP 2006-524515A (W02005/065116)
Patent Document 3: JP 2009-515654A (W02007/059189)

DISCLOSURE OF THE INVENTION

Problems to be Solved by the Invention

During use of the laser treatment apparatus having the binocular indirect ophthalmoscope attached with the irradiation optical system as disclosed in Patent Document 3, an operator has to hold an optometry lens for observation by hand and move his/her head for alignment of a laser irradiation position with respect to a patient's eye. However, it is not easy for the operator to appropriately align an irradiation position of a laser beam to a target affected part by moving his/her head while observing the patient's eye through the optometry lens. This operation requires a lot of skill. Further, the binocular indirect ophthalmoscope having the irradiation optical system in which the scanning unit is installed is apt to be unbalanced when worn on the head, so that the spot of the laser beam is liable to deviate from a target point during scanning of the laser beam.

The present invention has been made to solve the above problems and has a purpose to provide an ophthalmic laser treatment apparatus capable of facilitating positioning of an irradiation position of a laser beam even with respect to a recumbent patient and performing appropriate treatment by scanning of the laser beam in the form of a spot beam.

Means of Solving the Problems

To achieve the above purpose, one aspect of the invention provides an ophthalmic laser treatment apparatus for treating a patient's eye by delivering and irradiating a laser beam to the eye, the apparatus comprising: a main unit; a laser source that is contained in the main unit and emits a laser beam for treatment; a hand-held cabinet provided separately from the main unit, the hand-held cabinet being able to be hand-held by a hand of an operator; a laser delivery optical system for irradiating the laser beam in a predetermined irradiation pattern onto tissues of the patient's eye, the laser delivery optical system including: a fiber unit connecting the hand-held cabinet to the main unit to deliver the laser beam emitted from the laser source to the patient's eye; a scanner for deflecting an optical axis of the laser beam; and an image forming optical system for forming an image of the laser beam in the form of a spot on the tissues of the patient's eye; an irradiation pattern setting unit for setting an irradiation pattern of the treatment laser beam; a control unit for controlling drive of the scanner based on a setting signal input through the irradiation pattern setting unit; and a beam combiner provided in the hand-held cabinet to make an observation optical path and an optical path of the laser delivery optical system coincident with each other.

Effects of the Invention

According to the present invention, it is possible to facilitate positioning of an irradiation position of a laser beam even with respect to a recumbent patient and perform appropriate treatment by scanning of the laser beam in the form of a spot beam.

MODE FOR CARRYING OUT THE INVENTION

Figure 1:
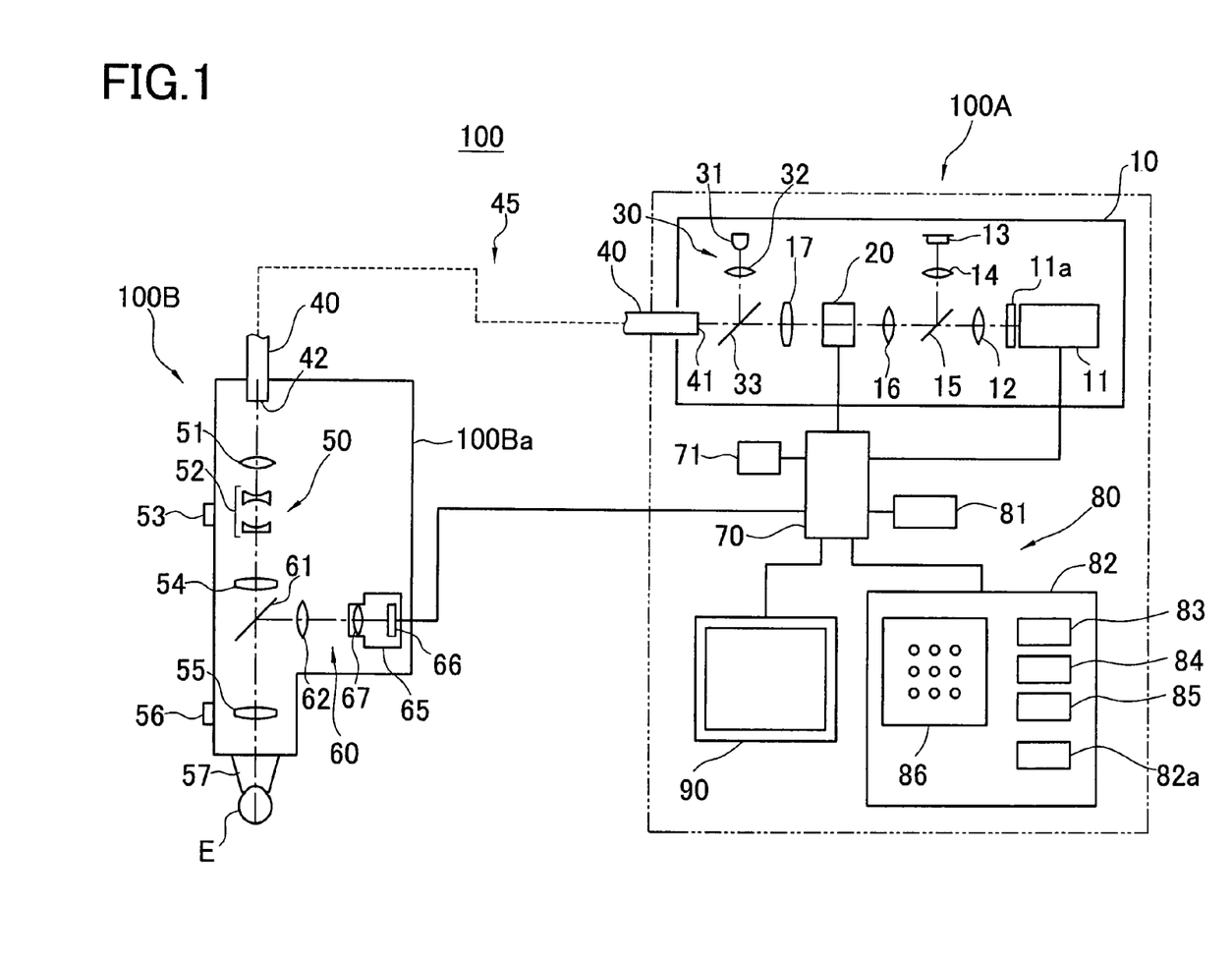
FIG. 1 is a schematic configuration view of optical systems and a control system of an ophthalmic laser treatment apparatus in an embodiment.
Figure 2A:
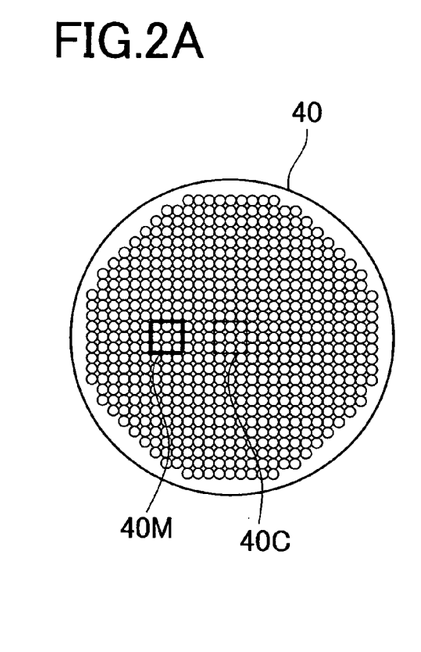
FIG. 2A is a diagram to explain the structure of a fiber bundle.
Figure 2B:
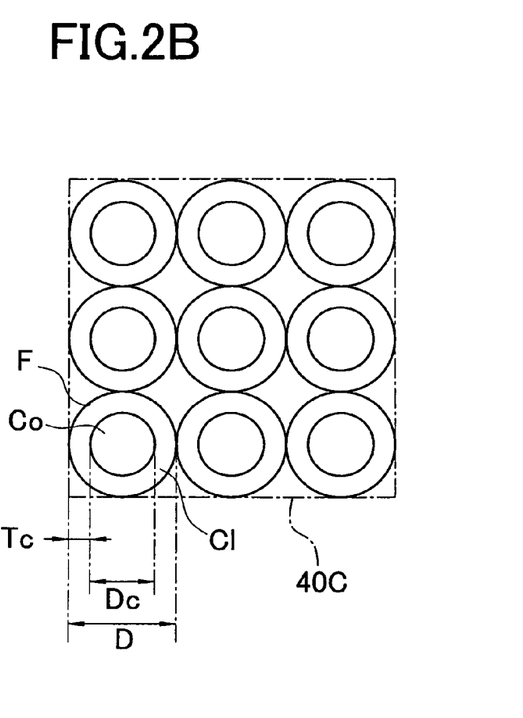
FIG. 2B is an enlarged diagram to show a central part of the fiber bundle of FIG. 2A.
Figure 3:
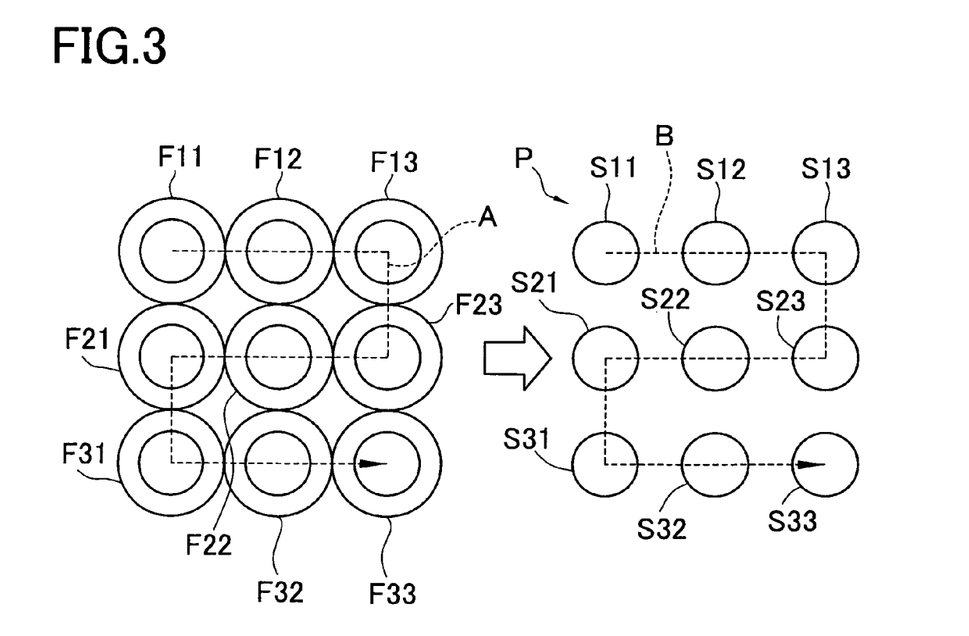
FIG. 3 is a diagram to explain an irradiation pattern.
Figure 4:
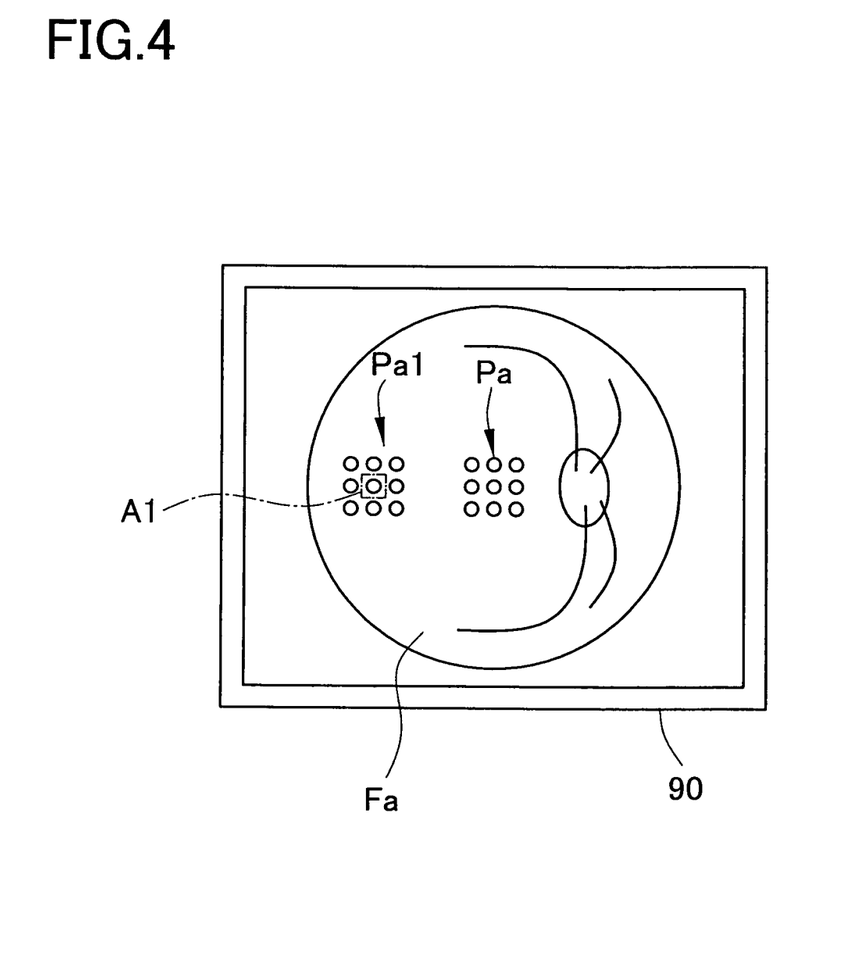
FIG. 4 is a diagram to explain a structure of a display.

A detailed description of a preferred embodiment of the present invention will now be given referring to the accompanying drawings. FIG. 1 is a schematic configuration view showing optical systems and a control system of an ophthalmic laser treatment apparatus arranged to irradiate a treatment laser beam to a fundus to perform a photocoagulation treatment or the like. FIG. 2A is a diagram to explain the structure of a fiber bundle (bundled fibers) included in a light delivery optical system for delivering the treatment laser beam. FIG. 2B is an enlarged diagram to show a central part of the fiber bundle of FIG. 2A. FIG. 3 is a diagram to explain one example of an irradiation pattern. FIG. 4 is a diagram to explain an observation image of the fundus of a patient's eye displayed on a display and how to designate an irradiation position of the treatment laser beam.

An ophthalmic laser treatment apparatus 100 mainly includes a main unit 100A and a hand piece 100B. The main unit 100A contains a treatment laser source 11 and others and is arranged to perform settings of the apparatus 100. The hand piece 100B has a hand-held cabinet 100Ba configured to be held by an operator's hand and contains an observation optical system 60 for observation of the patient's eye and an irradiation optical system 50 for irradiating a laser beam to the patient's eye E. The laser beam from a treatment laser source 11 passes through a light delivery optical system 45 such as a fiber bundle 40, the irradiation optical system 50 including a contact lens 57 serving as an optometry lens provided in the hand piece 100B, and others, and is irradiated to the patient's eye. Specifically, the main unit 100A includes an illumination optical system 30, a control unit 70, an operation unit 80, and a display 90. The hand piece 100B includes the irradiation optical system 50 and the observation optical system 60 including a camera 65. The irradiation optical system 50 and the observation optical system 60 are contained in the cabinet (housing) 100Ba of the hand piece 100B. An entrance (incident) end of the fiber bundle 40 is connected to the main unit 100A and an exit (emission) end of the fiber bundle 40 is connected to the irradiation optical system 50 of the hand piece 100B.

The laser source unit 10 includes a treatment laser source 11 that emits a treatment laser beam, a condensing lens 12, a safety shutter 11a, an aiming light source 13 that emits an aiming laser beam (an aiming beam) to allow an operator to check a spot position, a condensing lens 14, a beam splitter (combiner) 15 that combines the treatment laser beam and the aiming beam (into coaxial beams), a lens 16 serving as an optical system for making the laser beam into almost parallel light, a scanning unit (a scanner) 20 provided with two galvano mirrors with their axes intersecting at a right angle in order to scan (deflect) an incident laser beam (an optical axis thereof) in two-dimensional directions, and a lens 17 for condensing the scanning laser beam on an entrance end face 41 of the fiber bundle 40. The light delivery optical system 45 of the main unit 100A includes the safety shutter 11a, the condensing lens 12, the lens 16, the scanning unit 20, and the lens 17. Further, the laser source unit 10 further includes the illumination optical system 30. The illumination optical system 30 includes an illumination light source 31 that emits infrared light, a lens 32 serving as an optical system for delivering illumination light to the entrance end face 41 of the fiber bundle 40, and a dichroic mirror 33 for combining the illumination light with the laser beam (to be coaxial with the laser beam).

The treatment laser source 11 may be selected from a semiconductor laser, a fiber laser, a solid laser, or the like, which are arranged to emit a visible laser beam suitable for fundus treatment (e.g., photocoagulation treatment). As the aiming light source 13, a semiconductor laser that emits a visible laser beam recognizable to an operator is used. It is to be noted that the aiming beam may also be infrared light. For instance, in the case of utilizing a system capable of imaging and displaying infrared light, even when the aiming beam is infrared light, the operator is allowed to recognize the position of the aiming beam and others. The beam splitter 15 is a dichroic mirror that transmits the treatment laser beam while reflects the aiming beam. The safety shutter 11a can be inserted in an optical axis to interrupt the treatment laser beam. Each galvano mirror used in the scanning unit 20 includes a scan mirror having a reflection plane, a shaft supporting the mirror, and an actuator (a motor) for axially rotating the shaft. The galvano mirrors turn the angles of their scan mirrors based on a command of the control unit 70 as will be mentioned later. The scanning unit 20 scans (deflects) the optical axis of the laser beam two-dimensionally and makes the laser beam enter one fiber of the fiber bundle 40. For the scanning unit 20, the technique disclosed in JP 2001-149403A is available.

The illumination light source 31 is selected from a halogen lamp provided with an infrared filter that blocks visible light, a light-emitting diode that emits infrared light, and others. The lens 32 has the optical property of delivering illumination light from the illumination light source 31 to almost all the entire surface of the entrance end face 41 of the fiber bundle 40. The dichroic mirror 33 has the property of transmitting a laser beam (the treatment laser beam and the aiming beam) while reflects infrared light. Accordingly, even when the visible light is emitted from the illumination light source 31, this light is blocked (herein, transmitted) by the dichroic mirror 33.

FIG. 2A schematically shows a cross section of the entire fiber bundle (fiber unit) 40 and FIG. 2B shows an enlarged view of a central part (3×3 fibers F). The fiber bundle 40 is a light delivering member consisting of a number of fibers F regularly bundled in a predetermined pattern. Each fiber F includes a core Co through which a laser beam propagates and a clad Cl covering over the core Co. Each fiber F is designed such that a core diameter Dc is of the order of 10 to 400 μm and a thickness Tc of the clad Cl is of the order of 10 to 400 μm. Accordingly, a fiber diameter D is of the order of 20 to 800 μm. The fibers F are bundled so that their cores Co are arranged in a lattice-like pattern on the entrance end face 41 (or the exit end face 42) of the fiber bundle 40. The number of the fibers is determined to be enough to deliver laser spots in a predetermined pattern on a fundus and further sufficient to deliver illumination light to the fundus. Specifically, the number of the fibers is several tens to several tens of thousands. The entrance end face and the exit end face of the fiber bundle 40 are flat.

In the present embodiment, each fiber F is a multimode fiber having a core diameter Dc of 50 μm clad thickness Tc of 25 μm, and a fiber diameter D of 100 μm, and 3000 multimode fibers are arranged in a square lattice pattern. Thus, the cores Co are spaced at intervals of 50 μm. Each fiber F is fixed with a fixing member (adhesive and others) not shown to keep a bundled state (an arrangement pattern). For instance, the arrangement pattern of the fibers F is maintained as a squire lattice pattern over a central section 40C (near the optical axis) and an intermediate section 40M on a more outward side than the central section 40C. Preferably, the arrangement pattern of at least the fibers F to be used for delivering the treatment laser beam is maintained to be lattice-shaped. The entrance end face of each fiber F has been subjected to an anti-reflection treatment so as to effectively have a laser beam enter each fiber F. The entrance end of the fiber bundle 40 is connected to the laser source unit 10 (the main unit 100A) and the exit end of the same is connected to the hand piece 100B.

In the hand piece 100B, the irradiation optical system 50 has a function of forming an image of an exit end face 42 of the fiber bundle 40 (the exit end face of each fiber F) on the fundus of the patient's eye. The irradiation optical system 50 includes a lens 51 for making the laser beam emerging from the fiber bundle 40 into almost parallel light, a lens (group) 52 slidable along the optical axis to serve as a variable-power optical system for changing an image-forming power (magnification) of a laser spot to be image-formed on the fundus of the patient's eye, a knob 53 for moving the lens 52, a relay lens 54, a focusing lens 55 for moving back and forth an image-forming position of the exit end face 42 of the fiber bundle 40 along the optical axis, a knob 56 for moving the focusing lens 55, and a contact lens (an optometry lens) 57 that is an objective lens of the irradiation optical system 50 and is to be positioned to face the patient's eye and contact with an anterior segment thereof. The observation optical system 60 includes a beam splitter 61 for separating an observation beam (reflection light from the fundus) from the laser beam and the illumination beam, a lens 62, and the camera 65 downstream of the lens 62. The contact lens 57 is used in common between the irradiation optical system 50 and the observation optical system 60. The contact lens 57 serves as an image forming lens for forming an image of the laser beam in the form of a spot on tissues of the patient's eye.

The lens 52 and the focusing lens 55 are held respectively by lens cams (not shown) and caused to slide along the optical axis by operation of the knobs 53 and 56 respectively. Those knobs 53 and 56 are arranged on the surface of the cabinet 100Ba to facilitate operator's manipulation. In this embodiment, the knobs 53 and 56 are provided to protrude from the cabinet 100Ba. The irradiation optical system 50 forms an image of the laser beam on the fundus of the patient's eye E, that is, conjugates the exit end face 42 of the fiber bundle 40 with the fundus. The laser spot is consecutively changed in a range of magnifications from 1× to 10× (50 to 500 µm in a spot diameter) by movement of the lens 52. The irradiation optical system 50 delivers the illumination beam to the fundus. In the present embodiment, the illumination beam is delivered to the fundus without forming an image due to aberration of optical components of the irradiation optical system 50 and the like. Accordingly, the fundus is illuminated by diffused infrared light.

The camera 65 includes a two-dimensional imaging element 66 and an image-forming lens 67. The imaging element 66 has the property of being able to receive infrared light (reflection light of the illumination beam), i.e., the property of being sensitive to infrared light, and can receive at least an aiming beam, i.e., the property of being sensitive to the aiming beam. The imaging element 66 in this embodiment is a two-dimensional CCD (charge-coupled device) with sensitivity to light in a wider wavelength range from infrared light to visible light. A light-receiving plane of the imaging element 66 is placed at a position conjugate with the fundus of the patient's eye E via the image-forming lens 67, the lens 62, the focusing lens 55, and the contact lens 57. The beam splitter (beam combiner) 61 serves to make an optical path of the observation optical system and an optical path of the irradiation optical system coincident with each other. The beam splitter 61 has the property of transmitting a laser beam while half-transmitting and half-reflecting infrared light in order to minimize attenuation of the laser beam (especially, the treatment laser beam). The focusing lens 55 has a function to make adjustment (fine adjustment) of visibility of the patient's eye E and is caused to slide in an axis direction by operation of the knob 56. With the focusing lens 55, the fundus of the patient's eye E and the light-receiving plane of the imaging element 66 are placed in a conjugate relation, and the fundus of the patient's eye E and the exit end face 42 of the fiber bundle 40 in a conjugate relation.

The light delivery optical system 45 and the irradiation optical system 50 constitute a laser delivery to irradiate the laser beam of a predetermined irradiation pattern onto the tissues of the patient's eye E. The laser delivery optical system includes the fiber bundle 40 serving as a fiber unit for delivering the laser beam emitted from the laser source 11 to the patient's eye E, the scanning unit 20 for deflecting the optical axis of the laser beam, and the contact lens 57 which is the image forming optical system to form a spot image of the laser beam having a predetermined spot size on the tissues of the patient's eye E. Herein, the contact lens 57 is included in the irradiation optical system 50.

The control unit 70 that controls the overall apparatus is connected to a memory 71, the laser source 11, the aiming light source 13, the safety shutter 11a, the scanning unit 20, the imaging element 66, the operation unit 80 for setting irradiation conditions of the laser beam and others, the display 90 used for observation of the fundus of the patient's eye E, and a footswitch 81 serving as a trigger input device to irradiate the laser beam. Turning-on of the illumination light source 31 and adjustment of light quantity thereof are performed with a switch not shown.

The operation unit 80 includes a touch-panel display 82 also used for setting the laser irradiation conditions and changing and inputting the irradiation pattern. The display 82 is provided with various kinds of panel switches whereby the irradiation conditions (parameters) of the laser beam can be set. The display 82 has a graphical user interface function and is configured to allow a user to visually check and set numeric values and others. For items of the irradiation conditions, there are prepared a setting part 83 for setting the output power of a treatment laser beam, a setting part 84 for setting an irradiation time (a pulse width), a setting part 85 for setting a halt time (a time interval of irradiation of a treatment laser beam), a setting part 86 for setting an irradiation (scanning) pattern of a treatment laser beam (an arrangement pattern of spot positions of a treatment laser beam to be formed on the fundus), a menu switch 82a for calling up other setting parts or the like, etc.

By touching each item on the display 82, numeric values can be set. For instance, if the operator touches a setting part on the display 82, a pull-down menu appears to provide selectable numerals. When the operator selects one of the numerals, a set value in the relevant item is determined. Further, by touching a spot position on the setting part 86 displaying a pattern, the irradiation pattern can be selected, changed, or the like. For changing the irradiation pattern, for example, a 3×3 pattern is selected and then a center spot position thereof is touched. The touched spot disappears from the pattern. By this operation, a new pattern is set.

The control unit 70 drives the laser source 11 and the aiming light source 13 based on the set irradiation pattern to control emission and stop of the laser beam and also drives the scanning unit 20 to make the laser beam enter the fibers F according to the set pattern (the details will be mentioned later).

The display 90 serves to display a fundus image captured by the imaging element 66. The display 90 also has a touch panel function as with the display 82. By designating (touching) a position on the fundus image displayed on the display 90, the irradiation position of the irradiation pattern can be moved (the details will be mentioned later).

The irradiation pattern of the treatment laser beam will be explained below. FIG. 3 shows 3×3 fibers (nine fibers) and the irradiation pattern. The following explanation is given to an example of 3×3 fibers F (F11, F12, F13, F21, F22, F23, F31, F32, and F33) selected from the fiber bundle 40.

In the present embodiment, the laser beam to be made to enter the fiber bundle 40 is designated (selected) by the scanning unit 20, thereby forming the irradiation pattern based on the square lattice pattern of the fibers F. An incoming pattern of the laser beam on the entrance end face 41 of the fiber bundle 40 comes to be an outgoing pattern on the exit end face 42 of the fiber bundle 40. The light of this pattern is delivered (irradiated) to the fundus through the irradiation optical system 50, thus forming the irradiation pattern on the fundus.

It is herein assumed a case where the laser beam enters nine fibers F on the entrance end face 41 side. As indicated in an arrow A in FIG. 3, the laser beam is deflected by the scanning unit 20 to enter the fibers F11, F12, F13, F23, F22, F21, F31, F32, and F33 in this order.

The laser beam entering the fiber F 11 propagates through the core Co and emerges from the fiber F 11 on the exit end face 42 side. At that time, at the exit end of the fiber F11, a spot corresponding to the core diameter Dc is formed. Similarly, spots are sequentially formed on the exit end face 42 side through the fibers F12, F13, F23, F22, F21, F31, F32, and F33 in this order. The spots on the exit end face 42 are delivered (irradiated) onto the fundus of the patient's eye E through the aforementioned irradiation optical system 50.

As shown in FIG. 3, a pattern P on the fundus is formed from a spot S11 corresponding to the fiber F11 and subsequent spots (spots S12, S13, S23, S22, S21, S31, S32, S33) in the order shown by an arrow B. In the case where an image forming power is 1×, the spot size on the fundus is 50 μm equal to the core diameter Dc of the fiber F and the spot interval (between outlines of adjacent spots) is 50 μm equal to two times the thickness Tc of the clad Cl.

It is to be noted that when the image-forming power is changed by the irradiation optical system 50, the spot size and the spot interval are enlarged while keeping the aforementioned relation (50 μm:50 μm=1:1). Under the condition of the pattern P being set, when setting to cancel a spot position corresponding to the spot S22 is performed on the setting part 86, the control unit 70 controls the scanning unit 20 so that the laser beam does not enter the fiber F22. To add a spot position, on the other hand, an additional spot position of the pattern is set (by touching a blank portion) on the setting part 86. Thereby, the control unit 70 controls the scanning unit 20 to make the laser beam enter another fiber not shown. As above, a desired pattern can be set to irradiate the laser beam.

For the irradiation pattern, a plurality of patterns have been prepared in advance to allow an operator to select any one on the display 82. The irradiation pattern is changed according to the fiber or fibers F of the fiber bundle 40 on which the laser beam is made to enter. The square lattice pattern of the fibers F is a basic pattern. The memory 71 further stores various patterns such as a pattern of spot positions arranged in a square matrix of 2×2, 3×3, 4×4, or others (a square pattern); a pattern of spot positions arranged in a circular arc line (a circular arc pattern); a pattern of spot positions arranged in plural circular arc lines in a radially outward or inward direction (a fan-like pattern); a pattern of spot positions arranged in a circle (a circular pattern); a pattern of spot positions arranged in a segmented circle (a segmented circular pattern); and a straight pattern of spot positions arranged in a straight line. The irradiation pattern can be selected from a plurality of irradiation patterns stored in the memory 71 by operation of the setting part 86 and a selected one is displayed on a screen of the setting part 86.

Until the footswitch 81 is depressed by the operator, the control unit 70 controls the aiming light source 13 to continue turning on and controls the scanning unit 20 based on the pattern set on the setting part 86 to form a spot pattern of the aiming beam on the fundus. During irradiation of the aiming beam, scanning is conducted at a speed allowing the operator to simultaneously observe the spot positions of the irradiation pattern by persistence of operator's vision or scanning is conducted to allow the operator to intermittently observe the spot positions, thereby individually observing the spot positions of the irradiation pattern.

When the footswitch 81 is depressed by the operator, the control unit 70 irradiates the laser beam to form a spot pattern of the treatment laser beam on the fundus based on various parameters. The control unit 70 controls the laser source 11 and also controls the scanning unit 20 based on the set pattern to form the spot pattern of the treatment laser beam on the fundus.

Next, an explanation is given to how to designate (move) the position of an irradiation pattern using the display 90. The display 90 in FIG. 4 displays in real-time a fundus Fa of the patient's eye E captured by the camera 65. Further, on the display 90, a pattern Pa of the aiming beam formed on the fundus Fa is also displayed (reflected). Herein, the pattern Pa is a square pattern of a 3×3 matrix. The pattern Pa consists of nine fibers in the central section 40C of the fiber bundle 40. Therefore, the pattern Pa is formed in the central part of an observation region (a central part of the display 90). When a region Al on the display 90 is touched, the pattern of the aiming beam indicated by a pattern Pal is displayed on the display 90. The display 90 functions as a panel switch so that a touched point on the display 90 is input to the control unit 70. The region Al corresponds to a region in which a central part of the irradiation pattern is located. Based on an input signal from the display 90, the control unit 70 acquires a displacement (deviation) amount from the central section 40C of the fiber bundle 40. The control unit 70 changes the scanning amount of the scanning unit 20 based on the displacement amount to change target fibers in which the laser beam (the aiming beam) is made to enter. For instance, a selected region (corresponding to the central section 40C) of the nine (3×3) fibers F targeted by the scanning unit 20 are changed to a deviated region (corresponding to the intermediate section 40M) of nine (3×3) fibers F.

As above, the display 90 functions as a movement signal input unit to move the spots of the irradiation pattern. By touch input on the touch-panel display, a signal is input to represent information of the movement position to which the spots of the irradiation pattern are to be moved. As the movement signal input unit, an input member such as a lever may be used to input a movement signal.

Operations of the apparatus configured as above will be explained below. Herein, a treatment on a patient who is lying (a treatment at bedside) is exemplified. Prior to a surgery, an operator observes a patient's eye E. Specifically, the operator turns on the illumination light source 31, and holds the hand piece 100B and brings the contact lens 57 into contact with an anterior segment of the patient's eye E. The operator then makes focus adjustment by manipulating the knob 56 so that a fundus image of the eye E properly appears on the display 90. While observing the fundus displayed on the display 90, the operator sets the surgery conditions on the display 82 such as the irradiation pattern, the output power of a treatment laser beam, and the irradiation time of the laser beam at one spot. Further, by adjustment of the knob 53, the spot size of the treatment laser beam is set.

When the operator turns on the aiming beam, establishing an irradiation enabled state of the treatment laser beam, the control unit 70 controls the scanning unit 20 and others to form a pattern of spots by the aiming beam on the fundus. At that time, the operator checks the pattern displayed on the display 90. When the irradiation position is to be changed, the operator touches the fundus image on the display 90 to change the position (region) of the irradiation pattern. The control unit 70 controls the scanning unit 20 in correspondence with the position designated on the display 90 to change the irradiation position of the irradiation pattern. The position of the irradiation pattern is changed by scanning of the scanning unit 20 without needing movement of the hand piece 100B with respect to the patient's eye E. Therefore, the operator can stably and easily change the position of the irradiation pattern to a desired position while holding the hand piece 100B by hand in an easy-to-hold state.

After the completion of alignment, when the operator depresses the footswitch 81, irradiation of the treatment laser beam is started. Based on a trigger signal from the foot switch 81, the control unit 70 causes the light source 12 to stop emission of the aiming beam and the treatment laser source 11 to emit the treatment laser beam and also controls the scanning unit 20 to sequentially irradiate the treatment laser beam at each spot position. After all the spot positions are irradiated by the treatment laser beam, the control unit 70 starts irradiation of the aiming beam again according to the irradiation pattern. In this way, even for a recumbent patient, positioning of the irradiation position of a laser beam can be easily conducted, so that appropriate treatment can be performed by scanning the spot of the laser beam.

With the optical systems in FIG. 1, it is possible to irradiate a plurality of spots based on a predetermined pattern while suppressing an increase in size of the apparatus. To be concrete, since the scanning unit 20 is provided in the main unit 100A, a unit capable of performing both the fundus observation and the later treatment can be achieved as the hand piece 100B which can be hand-held. This facilitates observation and treatment at bedside. Since the hand piece 100B and the contact lens 57 are integral, the apparatus 100 can be easily handled. Further, such configuration makes it easy to press the contact lens 57 against the patient's eye.

Although the above explanation is given to the example of use of the apparatus at bedside, the present invention is not limited thereto. The observation and the treatment using the hand piece 100B may be performed to a patient who is in a sitting position. The hand piece 100B has only to be configured as an integral unit and may be mounted on a table provided with a head support unit.

In the above explanation, the scanning unit uses two galvano mirrors with their rotating axes intersecting with each other. The scanning unit has only to be configured to deflect (scan) a laser beam two-dimensionally and thus may also use a deflection unit utilizing the inclination of a lens or a deflection unit using a deformable mirror.

In the above explanation, infrared light is used as the illumination light. As an alternative, a light emission diode that emits visible light may be used as an illumination light source. In this case, the mirror 33 for making a laser beam and an illumination beam coaxial with each other is a dichroic mirror that transmits wavelengths of the aiming beam and the treatment laser beam while reflects the illumination light. This mirror needs the optical property of turning the color of the illumination light to nearly white.

In the above explanation, a zoom function is provided by sliding of the lens 52. However, the present invention is not limited thereto and any power-variable configuration may be adopted. For example, it may be configured to insert and remove an optical element with respect to the optical path of the irradiation optical system to thereby change an image forming power (magnification) of the spot.

Although the above explanation shows the use of fibers F each having a core diameter Dc of 50 μm and a clad thickness Tc of 25 μm, the present invention is not limited thereto. Further, the arrangement pattern is not limited to the square lattice pattern and may also be a hexagonal lattice pattern. It is to be noted that as long as the size of each fiber F is set to provide the spot size and the spot interval suitable for laser treatment, the variable power optical system is not indispensable. For instance, an arrangement of fibers each having a core diameter Dc of 200 μm and a clad thickness Tc of 100 μm arrayed in a square lattice pattern is a setting generally used for photocoagulation treatment.

Further, observation of the fundus is conducted by the camera 65 placed in the hand piece 100B in the above explanation but may also be performed by visual observation through the observation optical system 60. In this case, the illumination light source is a visible light source. As another alternative, it may be arranged to observe the fundus through the fiber bundle 40. The light receiving plane of the imaging element for observation of the fundus and the entrance end face 41 have only to be disposed in a conjugate relation.

In the above explanation, the objective lens serving as the optometry lens of the hand piece 100B is provided as the contact lens 57 which will be placed in contact with the patient's eye E. Instead of the contact lens 57, an optometry lens placed in a position facing and apart from the patient's eye E may be used. In this case, focus adjustment can be performed by moving the hand piece 100B in the optical axis direction and the aforementioned focus lens 55 is not indispensable.

In the above explanation, the position of the irradiation pattern is designated (changed) on the display 90. Without limiting the invention to this configuration, an input device such as a lever for inputting a signal to move the position of the irradiation pattern may be adopted. The control unit 70 may also be configured to control the scanning part 20 based on input from the input device to change a deflection direction (scanning direction) of the laser beam. In such a case, the display 90 may be arranged to directly display an image signal from the imaging element 66. Changing the position of the irradiation pattern of the laser beam may be carried out by inclining or moving the hand piece 100B relative to the patient's eye E. However, when the contact lens 57 is used, the hand piece 100B is hard to move. It is therefore preferable to change the position of the irradiation pattern by controlling the scanning unit 20. The irradiation pattern may also be provided as a fixed specific pattern previously set. For example, the apparatus may be initially set with a 2×2 square pattern.

A manipulator function may also be added to the above explained configuration. To be concrete, a configuration to finely adjust an irradiation position of a treatment laser beam (a laser optical axis) is provided somewhere on an optical path between the exit end face 42 of the fiber bundle 40 and the patient's eye E. For instance, a movement mechanism is provided to move the lens 54 laterally (in X-Y directions) with respect to the optical axis. In addition, an operation member such as a lever to be manipulated by an operator to operate this movement mechanism is placed on the hand piece 100B. By lever operation of the operator, the lens 54 is moved, inclining the laser optical axis. Accordingly, the position of the irradiation pattern on the fundus is wholly moved.

The lens 54 may also be configured to be inclined by the movement mechanism.

The irradiation optical system 50 and the observation optical system 60 are interchanged in arrangement so that the beam splitter 61 reflects the treatment laser beam and others while transmits the infrared light. Further, an inclination mechanism for inclining the beam splitter 61 in a lateral direction (X-Y directions) relative to the laser optical axis is provided and a lever to be manipulated by an operator to move this inclination mechanism is provided on the hand piece 100B. By operator's lever manipulation, the beam splitter 61 is inclined, thereby inclining the laser optical axis. Accordingly, the position of the irradiation pattern on the fundus is wholly moved.

The movement mechanism and the inclination mechanism mentioned above may be operated mechanically with a lever or the like or electrically with a drive unit such as an actuator. Such operations may be achieved by an operation part provided in other than the hand piece 100B, for example, by signal input to a monitor.

The movement mechanism and the inclination mechanism mentioned above may also be controlled by the control unit 70. For instance, the control unit 70 controls the movement mechanism (or the inclination mechanism) to displace or deviate the position of the entire irradiation pattern irradiated on the fundus by a certain distance (e.g., a distance corresponding to one spot) in any direction. Accordingly, the treatment laser beam can be irradiated at narrower space intervals than the intervals between the spots (the intervals between adjacent cores) with design limitation of the fiber bundle 40. When the movement mechanism and others are controlled to move the spot of the treatment laser beam, it is easy to form various irradiation patterns having a curved line such as a circular pattern.

The control unit 70 may also control the movement mechanism and others based on an image captured by the camera 65 to track the irradiation position of the treatment laser beam. For instance, the control unit 70 extracts a characteristic point of the fundus image and monitors the movement amount of the characteristic point. Specifically, the control unit 70 controls the movement mechanism and others based on the movement amount of the characteristic point and displaces the position of the spot of the treatment laser beam to cancel the motion of the fundus.

Figure 5:
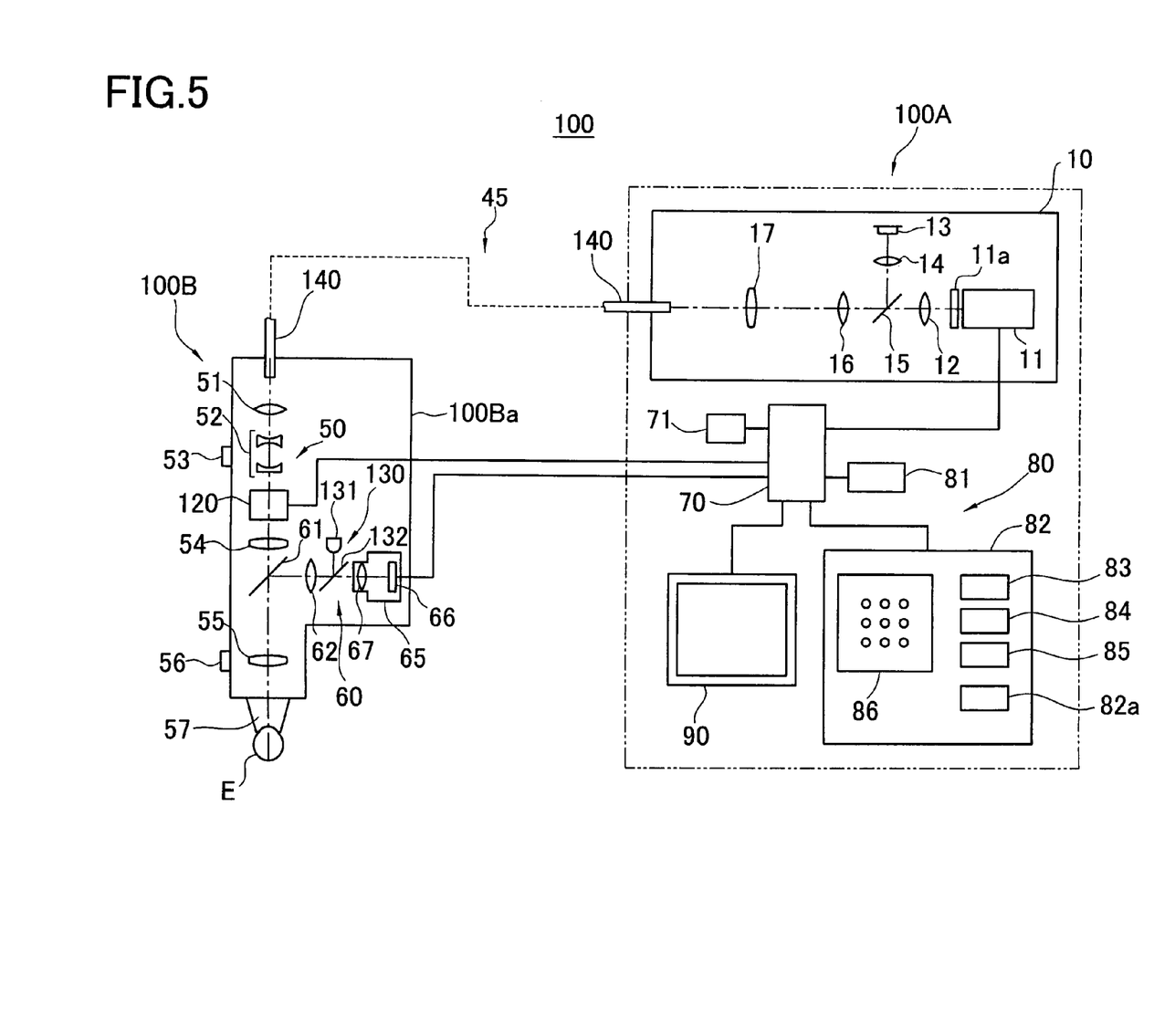
FIG. 5 is a schematic configuration view of a modified example of the ophthalmic laser treatment apparatus.

A modified example of the above embodiment is explained below referring to FIG. 5. FIG. 5 shows the modified example of the light delivery optical system in FIG. 1 and is a configuration view showing a case where a scanning unit (scanner) is provided in the irradiation optical system 50 of the hand piece 100B. A scanning unit 120 placed in the handheld cabinet 100Ba scans the laser beam emerging from a fiber 140 (deflects the optical axis of the laser beam). In FIG. 5, the scanning unit 120 consists of a scanning optical system such as galvano mirrors and others as in FIG. 1. The scanning unit 120 is placed between the lens (group) 52 and the relay lens 54. Instead of the fiber bundle 40, a single fiber 140 is connected to the main unit 100A and the hand piece 100B respectively. An illumination optical system 130 is provided in the hand piece 100B. This illumination optical system 130 includes an illumination light source 131 and a beam splitter 132 placed between the camera 65 and the lens 62 and also uses in common the lens 62, the beam splitter 61, the focusing lens 55, and the contact lens 57 of the observation optical system 60. The light delivery optical system of the main unit 100A does not include the scanning unit 20 and the dichroic mirror 33 shown in FIG. 1. Other parts or components are identical to those in FIG. 1 and hence their explanations are omitted by using the same reference signs as those in FIG. 1.

The fiber 140 is not limited to a single fiber and instead may be provided as a fiber unit consisting of a plurality of fibers. For instance, the fiber unit may include fibers having different core diameters. Thus, a spot size of the laser beam can be changed when the laser beam is made to enter one of the fibers of the fiber unit. In this case, a deflection unit such as a scanning unit or the like has to be provided at an entrance end side of the fiber unit in order to select the fiber in which the laser beam is to enter.

In the light delivery optical system in FIG. 5, a treatment laser beam and an aiming beam are delivered to the irradiation optical system 50 through the fiber 140 and directed by the scanning unit 120 to scan the patient's eye E. In the case of the light delivery optical system in FIG. 5, the scanning unit 120 is provided in the hand piece 100B and thus the size of the hand piece 100B is larger than that in FIG. 1. However, the light delivery optical system in FIG. 5 can provide such an advantage that it is possible to freely scan the position of a spot of a laser beam without being influenced by the arrangement pattern of the fibers of the fiber bundle 40 in FIG. 1. Therefore, the setting part 86 is configured to freely set the irradiation pattern such as the position of arrangement of the spots and the spot intervals. For laser irradiation, input of a movement signal to move the aiming light and control of driving the scanning unit 120 are substantially the same as in the case shown in FIG. 1 and thus their explanations are omitted herein.

The above explanation exemplifies that the hand piece 100B (the hand-held cabinet 100Ba) incorporates the observation optical system 60, but the present invention is not limited thereto. The hand-held cabinet 100Ba has only to be configured so that a beam combiner is placed in a position facing a patient's eye to make the optical path of the observation optical system and the optical path of the laser delivery optical system (the irradiation optical system) coincident with each other. For instance, as the observation optical system, a separate apparatus from the ophthalmic laser treatment apparatus, such as an operating microscope, may be utilized.

While the presently preferred embodiment of the present invention has been shown and described, it is to be understood that this disclosure is for the purpose of illustration and that various changes and modifications may be made without departing from the scope of the invention as set forth in the appended claims.

DESCRIPTION OF THE REFERENCE SIGNS

11 Treatment laser source
13 Aiming light source
20, 120 Scanning unit
30, 130 Illumination optical system
40 Fiber bundle
45 Light delivery optical system
50 Irradiation optical system
60 Observation optical system
70 Control part
80 Operation unit
90 Display
100 Ophthalmic laser treatment apparatus
100A Main unit
100B Hand piece
100Ba Handheld cabinet
140 Fiber

The invention claimed is:

1. An ophthalmic laser treatment apparatus for treating a patient's eye by delivering and irradiating a laser beam to the eye, the apparatus comprising:
a main unit;
a laser source that is contained in the main unit and emits a laser beam for treatment;
a hand-held cabinet provided separately from the main unit, the hand-held cabinet being able to be hand-held by a hand of an operator;
a laser delivery optical system for irradiating the laser beam in a predetermined irradiation pattern onto tissues of the patient's eye, the laser delivery optical system including:
a fiber unit connecting the hand-held cabinet to the main unit to deliver the laser beam emitted from the laser source to the patient's eye;
a scanner for deflecting an optical axis of the laser beam; and
an image forming optical system for forming an image of the laser beam in the form of a spot on the tissues of the patient's eye;
an irradiation pattern setting unit for setting an irradiation pattern of the treatment laser beam;
a control unit for controlling drive of the scanner based on a setting signal input through the irradiation pattern setting unit; and
a beam combiner provided in the hand-held cabinet to make an observation optical path and an optical path of the laser delivery optical system coincident with each other.

2. The ophthalmic laser treatment apparatus according to claim 1, wherein
the fiber unit is a fiber bundle including a number of fibers bundled in a predetermined pattern and having an entrance end connected to the main unit and an exit end connected to the hand-held cabinet,
the scanner is placed between the laser source and the entrance end of the fiber bundle, and
the control unit controls the drive of the scanner based on the setting signal input through the irradiation pattern setting unit to make the laser beam selectively enter in entrance ends of the fibers of the fiber bundle.

3. The ophthalmic laser treatment apparatus according to claim 1, further including a movement signal input unit including a switch for inputting a movement signal to move an irradiation position of the laser beam of the set irradiation pattern,
wherein the control unit controls the drive of the scanner based on the setting signal of the irradiation pattern setting unit and a movement signal input by the movement signal input unit.

4. The ophthalmic laser treatment apparatus according to claim 1, further including an aiming light source that is placed closer to the laser source side than the scanner is, the aiming light source being configured to emit an aiming beam to allow an operator to check an irradiation position of the laser beam,
wherein the control unit controls the drive of the scanner based on the irradiation pattern and a movement signal input by a movement signal input unit even during irradiation of the aiming beam.

5. The ophthalmic laser treatment apparatus according to claim 2, wherein
the irradiation pattern settable by the irradiation pattern setting unit is determined according to a pattern of the bundled fibers of the fiber bundle.

6. The ophthalmic laser treatment apparatus according to claim 2, further including:
an illumination light source provided in the main unit; and
an illumination optical system including a lens through which illumination light from the illumination light source is made to enter almost the whole of the entrance end of the fiber bundle to deliver the illumination light to the patient's eye by using the fiber bundle in common.

7. The ophthalmic laser treatment apparatus according to claim 1, wherein
the hand-held cabinet is provided with an observation optical system including an imaging element to image the patient's eye, and
the ophthalmic laser treatment apparatus includes a display for displaying an image of the patient's eye captured by the imaging element.

8. The ophthalmic laser treatment apparatus according to claim 7, wherein the observation optical system is also used as an image forming optical system.

9. The ophthalmic laser treatment apparatus according to claim 1, wherein
the scanner is provided in the hand-held cabinet to deflect the optical axis of the laser beam emerging from the fiber unit.

10. The ophthalmic laser treatment apparatus according to claim 9, wherein the fiber unit includes a substantially single fiber.

* * * * *